(12) United States Patent
Biss et al.

(10) Patent No.: US 8,460,390 B2
(45) Date of Patent: Jun. 11, 2013

(54) SYSTEM AND METHOD FOR REPLICATING ORTHOPAEDIC IMPLANT ORIENTATION

(75) Inventors: Matthew Biss, Paris, OH (US); Jack Long, Warsaw, IN (US); Edmund Frazee, Cromwell, IN (US)

(73) Assignee: DePuy Products, Inc., Warsaw, IN (US)

( * ) Notice: Subject to any disclaimer, the term of this patent is extended or adjusted under 35 U.S.C. 154(b) by 2282 days.

(21) Appl. No.: 11/025,223

(22) Filed: Dec. 29, 2004

(65) Prior Publication Data
US 2006/0142871 A1 Jun. 29, 2006

(51) Int. Cl.
*A61F 2/40* (2006.01)
(52) U.S. Cl.
USPC ............. 623/19.14; 623/22.46; 623/23.47
(58) Field of Classification Search
USPC .......... 623/19.14, 20.15, 22.41, 22.42, 22.43, 623/22.44, 22.45, 22.46, 23.44, 23.47, 19.11, 623/19.12, 19, 38; 403/90
See application file for complete search history.

(56) References Cited

U.S. PATENT DOCUMENTS

| | | |
|---|---|---|
| 4,003,095 A | 1/1977 | Gristina |
| 4,676,797 A | 6/1987 | Anapliotis et al. |
| 4,822,370 A | 4/1989 | Schelhas |
| 5,076,541 A | 12/1991 | Daghe et al. |
| 5,080,685 A | 1/1992 | Bolesky et al. |
| 5,314,479 A | 5/1994 | Rockwood, Jr. et al. |
| 5,358,526 A | 10/1994 | Tornier |
| 5,370,706 A | 12/1994 | Bolesky et al. |
| 5,702,457 A | 12/1997 | Walch et al. |
| 5,725,597 A | 3/1998 | Hwang |
| 5,741,335 A | 4/1998 | Gerber et al. |
| 5,743,898 A | 4/1998 | Bailey et al. |
| 5,910,143 A | 6/1999 | Cripe et al. |
| 6,197,062 B1 | 3/2001 | Fenlin |
| 6,203,575 B1 | 3/2001 | Farey |
| 6,206,925 B1 | 3/2001 | Tornier |
| 6,228,120 B1 | 5/2001 | Leonard et al. |
| 6,283,999 B1 | 9/2001 | Rockwood, Jr. |

(Continued)

FOREIGN PATENT DOCUMENTS

| | | |
|---|---|---|
| DE | 4445892 A1 | 6/1996 |
| DE | 19509037 C1 | 9/1996 |

(Continued)

OTHER PUBLICATIONS

DE 101 23 517 C1 (published on Nov. 28, 2002)—machine generated English language translation.*

(Continued)

*Primary Examiner* — David H. Willse
(74) *Attorney, Agent, or Firm* — Maginot, Moore & Beck, LLP

(57) ABSTRACT

A trial implant system includes a stem component and an articulating component forming part of a joint of a patient. A trial mounting assembly mounts the articulating component to the stem component at variable relative angular positions. The trial mounting assembly includes an expandable ball portion and an expansion element configured to expand the ball portion upon rotation of the expansion element. In an expanded state, the ball portion contacts a cavity within the stem at three points of contact to fix the center of rotation of the ball portion at a pre-determined location within the stem. The stem cavity defines an inwardly projecting circumferential lip that bears against ball portion as it expands to ensure the three-point contact.

20 Claims, 3 Drawing Sheets

U.S. PATENT DOCUMENTS

| | | |
|---|---|---|
| 6,328,748 B1 | 12/2001 | Hennig |
| 6,361,566 B1 | 3/2002 | Al-Hafez |
| 6,478,500 B1 | 11/2002 | Farenholtz |
| 6,558,425 B2 | 5/2003 | Rockwood, Jr. |
| 6,620,197 B2 | 9/2003 | Maroney et al. |
| 6,626,946 B1 | 9/2003 | Walch et al. |
| 6,673,114 B2 | 1/2004 | Hartdegen et al. |
| 6,736,851 B2 | 5/2004 | Maroney et al. |
| 6,736,852 B2 | 5/2004 | Callaway et al. |
| 6,749,637 B1 | 6/2004 | Bähler |
| 6,776,799 B2 * | 8/2004 | Ball et al. ............ 623/19.11 |
| 6,863,690 B2 | 3/2005 | Ball et al. |
| 6,953,478 B2 | 10/2005 | Bouttens et al. |
| 7,192,449 B1 | 3/2007 | McQueen et al. |
| 7,238,207 B2 | 7/2007 | Blatter et al. |
| 7,431,736 B2 | 10/2008 | Maroney et al. |
| 2001/0041940 A1 | 11/2001 | Pearl |
| 2001/0053935 A1 | 12/2001 | Hartdegen et al. |
| 2002/0016634 A1 | 2/2002 | Maroney et al. |
| 2003/0014112 A1 | 1/2003 | Ralph et al. |
| 2003/0040802 A1 | 2/2003 | Errico et al. |
| 2003/0097183 A1 | 5/2003 | Rauscher et al. |
| 2004/0002765 A1 | 1/2004 | Maroney et al. |
| 2004/0010261 A1 | 1/2004 | Hoag et al. |
| 2004/0030400 A1 | 2/2004 | Horber |
| 2004/0064142 A1 | 4/2004 | Ball et al. |
| 2004/0064188 A1 | 4/2004 | Ball et al. |
| 2004/0064189 A1 | 4/2004 | Maroney et al. |
| 2004/0122440 A1 | 6/2004 | Daniels et al. |
| 2004/0167629 A1 | 8/2004 | Geremakis et al. |
| 2005/0113931 A1 | 5/2005 | Horber |
| 2005/0143829 A1 | 6/2005 | Ondrla et al. |
| 2005/0149050 A1 | 7/2005 | Stifter et al. |
| 2005/0187637 A1 | 8/2005 | Karrer et al. |
| 2005/0251263 A1 | 11/2005 | Forrer et al. |
| 2005/0288681 A1 | 12/2005 | Klotz et al. |
| 2006/0142872 A1 | 6/2006 | Klotz et al. |
| 2007/0078519 A1 | 4/2007 | Klotz |
| 2007/0112430 A1 | 5/2007 | Simmen et al. |

FOREIGN PATENT DOCUMENTS

| | | |
|---|---|---|
| DE | 19951141 A1 | 5/2001 |
| DE | 101 23 517 | 11/2002 |
| DE | 202005020876 U1 | 10/2006 |
| EP | 0549480 A1 | 6/1993 |
| EP | 0679375 A1 | 11/1995 |
| EP | 0 712 617 | 5/1996 |
| EP | 0 715 836 | 6/1996 |
| EP | 0 931 522 | 7/1999 |
| EP | 1186278 A2 | 3/2002 |
| EP | 1 314 407 | 5/2003 |
| EP | 1 321 114 | 6/2003 |
| EP | 1 402 856 | 3/2004 |
| EP | 1393697 A1 | 3/2004 |
| EP | 1681037 A2 | 7/2006 |
| EP | 1769776 A1 | 4/2007 |
| FR | 2731612 A1 | 9/1996 |
| JP | 2004512922 A1 | 4/2004 |
| WO | 9303688 A1 | 3/1993 |
| WO | 0122905 A1 | 4/2001 |
| WO | 0239932 A1 | 5/2002 |
| WO | 03096870 A2 | 11/2003 |
| WO | 03096939 A1 | 11/2003 |

OTHER PUBLICATIONS

The McElroy Translation Company, English translation of German patent No. DE 101 23 517 C1, Jan. 2006 (20 pages).

Australian Search Report in Australian application AU2006225167, mailed Mar. 22, 2011 (2 pages).

Japan Patent Office, Notification of Reasons for Refusal (Translation) associated with patent application 2006-267228, mailing date Oct. 5, 2010 (4 pages).

European Search Report in European application EP06255073.6, mailed Jan. 5, 2007 (8 pages).

European Search Report in European application EP09162325.6, mailed Oct. 2, 2009 (6 pages).

European Search Report in related European patent application EP05257963.8, mailed Dec. 20, 2007 (5 pages).

Australian Search Report in related Australian patent application AU2005246996, mailed Apr. 27, 2010 (3 pages).

European Search Report in related European patent application EP10178881.8, mailed Mar. 10, 2011 (5 pages).

European Search Report in related European patent application EP10178895.8, mailed Dec. 14, 2010 ( 7 pages).

Japanese Office Action in related Japanese patent application JP2005-378997, mailed Feb. 9, 2010 (12 pages).

* cited by examiner

SYSTEM AND METHOD FOR REPLICATING ORTHOPAEDIC IMPLANT ORIENTATION

BACKGROUND OF THE INVENTION

1. Field of the Invention

The present invention relates to prosthetic devices and, more specifically, to a system and method for replication of angular position of an articulating head of a prosthesis. The invention has particular application to the humeral component of a shoulder prosthesis.

2. Background Information

Repair and replacement of human joints, such as the knee, shoulder, elbow and hip, has become a more and more frequent medical treatment. Longer life spans mean that the joints endure more wear and tear. More sports activities mean greater likelihood of serious joint injuries. Treatment of injuries, wear and disease in human joints has progressed from the use of orthotics to mask the problem, to fusion of the joint, to the use of prostheses to replace the damaged joint component(s).

As the success rate for total or partial joint replacements has increased, so too has the need for modularity and universality in the joint prosthesis. Patient variety means that no single size or configuration of joint prosthesis will suffice. The physical dimensions of a patient's joint components vary, as well as the bio-mechanic relationship between these components. For instance, in a shoulder prosthesis, the relationship between the articulating humeral and glenoid components can be significantly different between patients. These relationships are especially important where only one component of the joint is being replaced and must integrate with the existing natural opposing joint component.

For instance, in many shoulder surgeries, only the humeral component is replaced, leaving the glenoid component intact. In this case, it is imperative that the articulating surface of the humeral component match the articulating surface of the glenoid component as perfectly as possible, both statically and dynamically. With a typical humeral prosthesis, version and inclination are adjusted by the geometry of the head of the prosthesis. In other words, certain pre-determined head geometries are available that can be selected for a mating glenoid component. Absent an infinite variety of pre-determined head geometries, the resulting humeral prosthesis can often only achieve a best-fit relationship to the glenoid component of the shoulder joint.

Presently, two strategies are available to a surgeon for shoulder replacement surgery. One strategy is to perform the shoulder replacement surgery in accordance with the design of a particular manufacturer's shoulder prosthesis or shoulder prosthesis product line. In this case, a surgeon is provided with instrumentation and technique guidelines for the particular shoulder prosthesis or prosthesis line. The guidelines and/or instrumentation direct or dictate the angle of humeral head resection for the implant (prosthesis). This angle is in relation to the humeral intramedullary canal and is designed to match an optimum set of angles already present in the design of the prosthesis.

Another approach is to perform the shoulder replacement surgery in accordance with the patient's anatomy. Particularly, the humeral head is resected according to angles perceived to be "anatomic" in the opinion of the surgeon, not according to angles already present in the prosthesis itself. With this approach, the prosthesis is designed so that its configuration is intraoperatively adjustable. This allows the prosthesis to be adjustable in situ so that it can match the bony preparation.

Even with respect to these two divergent manners of surgical strategy, a common problem in shoulder surgery is matching the humeral resection angle across the articular margin to the predetermined angle designed into the prosthesis. This angle may include the angle between a prosthetic collar and the diaphyseal section of the stem. In the case of a collarless stem, the angle may inscribe the difference between the longitudinal axis of the stem and the inferior surface of the prosthetic head. It is considered optimal for fixation and biomechanics if the resected angle and the angle of the prosthesis are identical, thereby allowing intimate contact between the superior surface of the resected bone and the inferior surface of the implant.

Moreover, the angular version in which the prosthesis is implanted will have a significant impact on the biomechanics of the prosthetic joint. Many shoulder prosthesis systems on the market dictate the varus/valgus angle of the bone cut. This strategy does not allow the surgeon to intraoperatively match the implant to the patient's biomechanics after the prosthesis has been trialed, much less implanted. There are two known products currently marketed that attempt to resolve at least one of the above-noted issues. First, the Tornier-Aequalis system provides a modular junction within the metaphyseal region of the stem which allows a small block between the stem and humeral head to be interchanged. This block is available in multiple angles, thus allowing the surgeon to select the block that best fits the bony anatomy as resected. This system, however, has two primary weaknesses. First, the use of modular blocks obviously forces the design to only allow angular adjustments in finite increments. Second, the need to adjust the angle through modular blocks forces the surgeon to remove the stem, change out a component, and reset the stem.

A second product currently marketed provides a humeral head that is infinitely adjustable in varus/valgus and anterior/posterior angles relative to the stem portion of the prosthesis. This is accomplished through a spherical shaped protrusion on the superior surface of the stem that fits into a spherical recess in the humeral head. These mating surfaces allow the head to be articulated about the stem, thus allowing adjustable positioning of the head. The head can be locked in a position relative to the stem. This solution provides the ability to adjust the neck-shaft angle as well as the version through flexibility in the anterior/posterior angle. The locking mechanism, however, is sub-optimal since it requires the turning of a locking screw that has its head facing lateral and inferior, for which there is no access once the stem has been cemented. This eliminates the ability to adjust head position on the fly, and forces a total revision if articular surfaces ever need to be revised. Lastly, the protrusion on the humeral stem even when the humeral head is not in place limits the surgeon's access to the glenoid in preparation for a glenoid replacement.

An improvement to this latter product places an adjustable mounting element between the stem and the humeral head. The mounting element is configured for articulating engagement with the stem to permit angular positioning of the head component in multiple degrees of freedom. Details of this prosthesis are found in co-pending application Ser. No. 10/748,448 (the '448 application), entitled JOINT PROSTHESIS WITH INFINITELY POSITIONABLE HEAD, filed on Dec. 30, 2003, and owned by the assignee of the present invention, the disclosure of which is incorporated herein by reference.

As disclosed in the '448 application, the humeral head is fixed to the mounting element by a press-fit engagement. The mounting element is fastened to the humeral stem by two mechanisms. In the first mechanism, the mounting element achieves a friction fit with a tapered bore in the neck of the humeral stem. The second fixation mechanism includes a screw that is threaded into a threaded bore portion of the tapered bore in the stem. The screw bears against the mounting element to lock the element in position within the tapered bore. The joint prosthesis in this '448 application is both modular and universal in that it permits infinitely variable positioning of a mating joint component relative to a bone engaging portion of the prosthesis. Moreover, this improved prosthesis is readily available for modification, whether during initial implantation or during a subsequent revision procedure.

With shoulder prostheses that allow a surgeon to adjust the angular position of the humeral head, such as those described above, a method must be available for trialing the prosthesis. When the trial prosthesis is implanted, several adjustments may be made to set the angular position of the prosthetic head relative to the humeral stem. In a typical trialing system, the trial prosthesis includes a broach configured to be tightly received within a previously prepared intramedullary (IM) canal of the humerus. In current systems, an articulating element is oriented relative to the neck of the broach and locked in place by a press-fit taper. Locking the articulating trial element thus requires impaction of the element within the broach. This method produces galling of the broach which can significantly limit the useful life of the broach. Moreover, the impaction step frequently causes the trial broach to sink further into the IM canal. This displacement of the trial broach results in an indeterminate offset of the center of rotation of the trial element. In addition, discrepancies between the amount of impaction of the trial element vis-à-vis the final implant element results in an unknown offset of this center of rotation, which ultimately leads to a poor anatomic fit and improper alignment of the humeral head prosthesis.

There is a need for a trialing system that avoids these problems of the current trialing approaches. There is a further need for a trialing system that can ensure accurate duplication of the angles of the trial implant without using impaction to fix the trial components.

SUMMARY OF THE INVENTION

These and other needs are met by the trial system and method of the present invention. In one embodiment, this trial system includes a trial implant for the joint of a patient, comprising a stem component configured for placement within a bone of a patient, an articulating component configured for articulating contact with a mating aspect of the joint, and a mounting assembly for mounting the articulating component to the stem component at variable angular orientations relative thereto. The mounting assembly includes a cavity defined in the stem portion, a mounting element having a portion configured to support the articulating component and an expandable portion configured to expand within the cavity, and an expansion element rotatable within the mounting element and cooperating with the expandable portion upon rotation to expand the expandable portion within the cavity.

In certain embodiment, the expandable portion of the mounting element includes an expanding ball and a bore within the ball. In one feature of these embodiments, mating portions of the expansion element and the bore define a rotational engagement so that rotation of the expansion element drives the expansion element into the bore. In addition, the expansion element and the bore include cooperating portions that cooperate to expand the ball when the expansion element is driven into the bore. In a more specific embodiment, the bore is a tapered threaded bore and the expansion element is a screw configured to be threaded into the threaded bore. Alternatively, the screw can be tapered to expand the bore and the ball. In another specific embodiment, the mating portions define a threaded engagement and the cooperating portions include a tapered portion of the bore and a peg on the expansion element sized to expand the tapered portion when the expansion element is driven into the bore.

In a further feature of the invention, the expanding ball includes a first ball portion adjacent the portion of the mounting element configured to support the articulating component defining a first spherical diameter. The ball portion further includes a second ball portion attached to the first ball portion and defining a second spherical diameter smaller than the first spherical diameter.

According to one novel aspect, the cavity in the stem includes an annular rim extending into the cavity. The annular rim defines an inner diameter that is less than the outer diameter of the expandable portion of the mounting element in both its un-expanded and expanded states. The expandable portion has a contracted state that defines an outer diameter less than the inner diameter of the rim so that the expandable portion can be inserted past the rim into the cavity. Once past the rim, the expandable portion may assume its un-expanded configuration in which the portion is trapped within the cavity but still movable to various angular orientations.

The invention further contemplates an improvement for a trial implant for the joint of a patient, the trial implant including a stem component configured for placement within a bone of a patient, an articulating component configured for articulating contact with a mating aspect of the joint and a mounting assembly for mounting the articulating component to the stem component at variable angular orientations. In accordance with one aspect of the invention, the improvement comprises a cavity defined in the stem portion, the cavity including a side wall, a base and an annular rim extending into the cavity opposite the base, and an expandable portion on the mounting assembly having an expanded configuration within the cavity in which the expandable portion is in contact with each of the side wall, base and annular rim of the cavity.

Preferably, the annular rim defines an inner diameter and the expandable portion defines an expanded diameter in the expanded configuration that is greater than the inner diameter. Moreover, the expandable portion has an unexpanded configuration defining a diameter greater than the inner diameter to retain the expandable portion within the cavity. In yet another aspect of this embodiment, the expandable portion has a compressed configuration defining a diameter that is less than the inner diameter to permit passage of the expandable portion past the annular rim into the cavity.

In accordance with certain aspects of this improvement, the expandable portion includes an expanding ball and an expansion element extending into the expanding ball and configured to expand the ball to the expanded configuration. The expanding ball may define a tapered threaded bore and the expansion element is a screw configured to be threaded into the threaded bore. in a preferred embodiment, the expanding ball includes a first ball portion arranged to contact the annular rim and the side wall when the expandable portion is expanded within the cavity and defining a first spherical diameter. The expanding ball further includes a second ball portion connected to the first ball portion and arranged to contact the base of the cavity when the expandable portion is expanded within the cavity and defining a second spherical diameter less than the first spherical diameter.

The invention also contemplates a method for establishing an angular orientation of an articulating component of an implant for the joint of a patient relative to a stem component configured for placement within a bone of a patient, comprising the steps of:

provi ding a trial mounting assembly for mounting the articulating component to the stem component, the trial mounting assembly having an expandable portion configured to expand within a cavity defined in the stem component;

disposing the expandable portion within the cavity in the stem component;

introducing an expansion element into the expandable portion;

rotating the expansion element relative to the expandable portion to drive the expansion element into the expandable portion causing the expandable portion to expand within the cavity.

Another method of the invention is directed to establishing an angular orientation of an articulating component of an implant for the joint of a patient relative to a stem component configured for placement within a bone of a patient, and comprises the steps of:

providing a trial mounting assembly for mounting the articulating component to the stem component, the trial mounting assembly having an expandable portion configured to expand within a cavity defined in the stem component;

disposing the expandable portion within the cavity in the stem component;

expanding the expandable portion within the cavity so that the expandable portion contacts the cavity at three points of contact.

It is one object of the invention to provide a trial system for use in obtaining the angular orientation of an articulating component for a joint prosthesis. Another object is to provide such as system that does not require impaction to fix the trial components in their proper angular orientation. Other objects and specific benefits of the invention can be discerned from the following written description and the accompanying figures.

DESCRIPTION OF THE PREFERRED EMBODIMENTS

Figure 1:
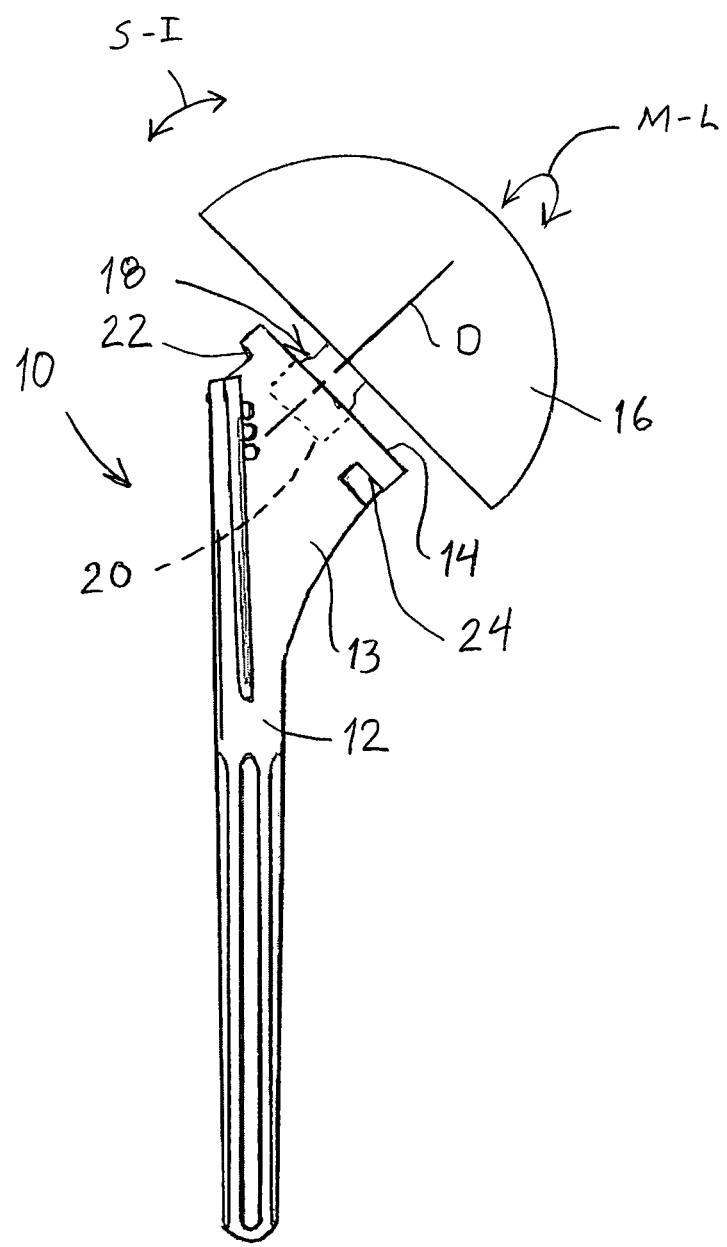
FIG. 1 is a side view of a humeral implant for a shoulder prosthesis.

While the invention is susceptible to various modifications and alternative forms, specific embodiments thereof have been shown by way of example in the drawings and will herein be described in detail. It should be understood, however, that there is no intent to limit the invention to the particular forms disclosed, but on the contrary, the intention is to cover all modifications, equivalents, and alternatives falling within the spirit and scope of the invention.

For purposes of illustration, the preferred embodiment of the invention is described in connection with a shoulder prosthesis, and particularly the humeral component of the prosthesis. However, the inventive concepts disclosed herein can be used at other joints or bone interfaces of the body. The common feature among these alternative uses of the invention is that they include components that can assume a range of angular orientations relative to each other—angular orientations that must be duplicated from a trial implant or prosthesis to a final implant.

As shown in FIG. 1, the present invention has particular application to a humeral prosthesis 10 for use in a shoulder joint replacement. The prosthesis includes a stem 12 configured to be disposed within the prepared IM canal of the humerus bone. Where the prosthesis 10 is a final implant, the stem is configured for permanent implantation within the IM canal, often accompanied by the introduction of bone cement into the canal. Where the prosthesis 10 is a trial implant, the prosthesis may be a broach that combines its function as a bone working tool to prepare the bore in the IM canal with its function as a trial stem.

The prosthesis 10 includes a neck 13 that is angled relative to the stem but arranged to sit flush with the resected head of the humerus bone when the prosthesis is implanted. An articulating head component 16, or humeral head for a shoulder prosthesis, is supported on the stem 12 by a mounting assembly 18. Where the prosthesis is a final prosthesis, the mounting assembly is configured for a final fixation, such as by impaction into a cavity 20 in the neck 13 of the stem. Where the prosthesis 10 is a trial broach, the mounting assembly 18 can be constructed according to the present invention disclosed herein.

In order to achieve a joint prosthesis that emulates the natural joint as closely as possible, the articulating component 16 is infinitely positionable. Where the prosthesis 10 is a humeral prosthesis, the humeral head component 16 must be variably angularly positionable in the medial-lateral M-L rotation and superior inferior S-I rotation degrees of freedom. In a typical shoulder joint, the humeral head will be positioned at an angle of 135° to the axis of the humerus bone. However, normal variations in patient anatomy can yield humeral head angles of 120°-150°. Thus, a universal humeral prosthesis 10 will be capable of 15° variations in all angular directions from the mean datum line D passing perpendicular to the platform surface 14 of the neck 13.

The neck 13 of the stem 12 includes a superior positioning groove 22 and a pair of inferior positioning grooves 24. As explained in more detail herein, these grooves establish the position of the trial and final implants in a replication instrument, serving as a means to provide a repeatable orientation for the datum line D relative to which the humeral head angular orientation is established.

Figure 2:
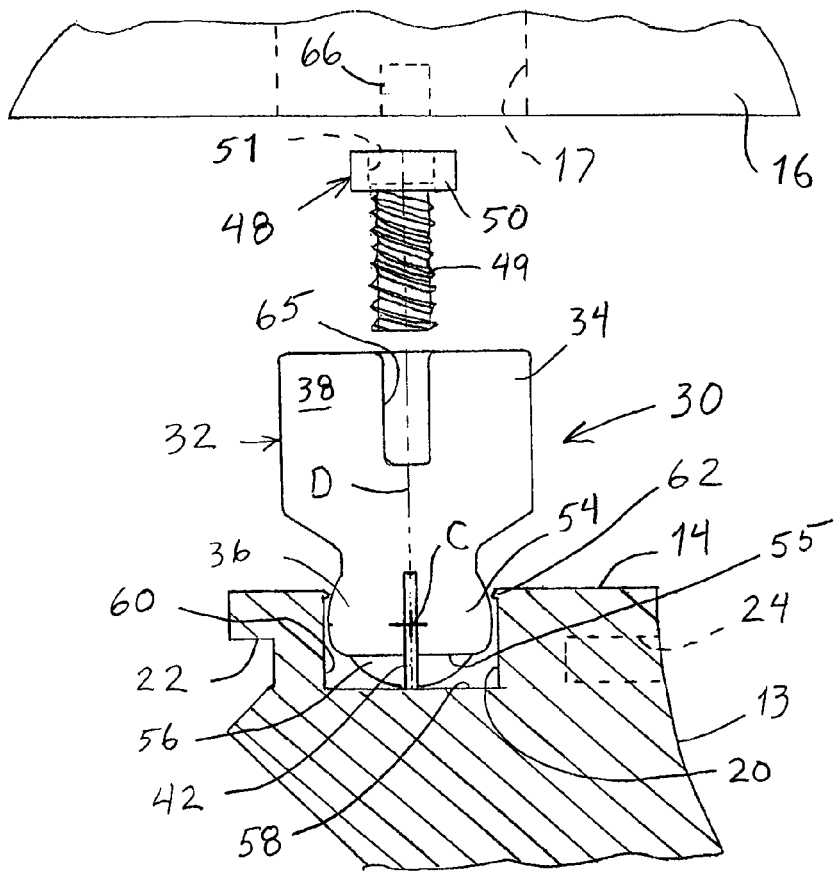
FIG. 2 is an enlarged partial cross-section view of a trial assembly in accordance with one embodiment of the present invention.

In accordance with the present invention, a trial assembly 30 is provided that does not require impaction of the trial components, as depicted in FIG. 2. The assembly 30 includes a trial ball cylinder 32 having a cylinder portion 34 and an expanding ball portion 36. The cylinder portion 34 defines an outer surface 38 that is received within a mating recess 17 formed in the humeral head component 16. Preferably, the cylinder portion and mating recess form a tight fit, but not a press-fit engagement so that no impaction of the trial assembly 30 is required. The cylinder portion 34 can be provided with an alignment notch 65 to receive a tab 66 formed on the interior of the mating recess 17 in the humeral head. The notch and tab interlock to ensure that the trial ball cylinder 32 rotates and pivots with the humeral head as the head is manipulated within the patient's shoulder joint to find the optimum fit with the glenoid aspect of the joint.

The trial ball cylinder defines an inner cavity 40 which provides access to a tapered bore 45. The tapered bore is coincident with expansion slots 42 formed in the expanding ball portion 36. In accordance with the preferred embodiment, four such expansion slots 42 are provided, as best seen in FIG. 4. The slots are configured in a conventional manner to allow the radial or diametrical expansion of the ball portion 32 as an expansion element is driven into the tapered bore 45. In the preferred embodiment, the expansion element is an expansion screw 48 with a uniform diameter threaded stem 49 that is threaded into internal threads 46 of the tapered bore. The screw 48 includes a head portion 50 that is preferably larger than the threaded stem 49 so the head portion contacts the angled portion 41 (FIG. 3) of the cavity to limit the passage of the screw into the bore. The head portion may be provided with an internal hex recess to receive a known hex driving tool for screwing the expansion element 48 into the tapered threaded bore 45.

Figure 5:
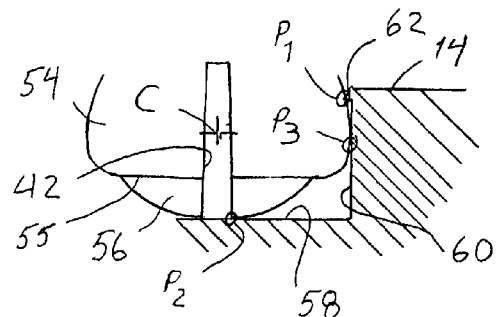
FIG. 5 is an enlarged partial cross-section view of the interface between the ball cylinder of FIG. 2 and the neck of a trial broach in accordance with one aspect of the present invention.

It should be readily understood that as the expansion screw 48 is threaded into the tapered bore 45, the threaded stem 49 causes the walls of the bore to expand outward, thereby opening each of the expansion slots 42 (as shown in FIG. 5). In accordance with the preferred embodiment of the invention, the expansion element 48 is a screw driven into a tapered bore. Alternatively, the bore 45 in the expanding ball portion 36 can have a uniform diameter and the expansion screw can incorporate a tapered threaded stem. Regardless of which component is tapered or uniform, a screw-threaded bore interface is a preferred mechanism to enlarge the expanding ball portion 36 since it relies upon the application of torque rather than on an impact force to drive the expansion element 48 into the bore 45. Other expansion elements are contemplated that rely upon the application of a torque or rotational force to expand the slots 42 in the ball portion 36.

In accordance with one feature of the trial assembly 30, the expanding ball portion 36 is configured so that the center of rotation C (FIGS. 2 and 5) will automatically substantially coincide with the center of rotation of the final implant. Ideally, this center of rotation C is fixed relative to the humerus bone when either the trial broach or the final implant is engaged with the IM canal. Maintaining this reference point constant ensures that the replicated angle of the humeral head in the final implant is anatomically accurate and appropriate for the patient's shoulder joint anatomy. As is apparent, the expanding ball portion 36 of the trial ball cylinder 32 is sized to freely slide in and out of the mounting cavity 20 formed in the neck 13 of the trial broach. Thus, unless the expanding ball portion is properly positioned and constrained, the center of rotation C can shift up and down and radially side to side within the cavity.

In one feature of the present invention, the expanding ball portion is positively positioned and constrained at three points of contact within the cavity 20. In accordance with the preferred embodiment, the expanding ball portion includes a larger ball portion 54 and a smaller ball portion 56 projecting from a truncated base 55 (FIGS. 1 and 5) of the larger ball portion. The two ball portions share their origin with the center of rotation C. The smaller ball portion 56 is provided to reduce the overall height of the expanding ball portion 36, which translates into a minimized depth for the mounting cavity 20. As can be seen in FIG. 1, the size of the neck 13 limits the depth for the mounting cavity 20. On the other hand, strength, stability and accuracy considerations suggest an optimum diameter for the expanding ball portion, and particularly for the larger ball portion 54. If the entire expanding ball portion 36 were formed at the same diameter as the larger ball portion, the cavity 20 would have to be deeper to accommodate the ball portion, which necessarily would exceed the structural limit for the cavity. Thus, truncating the larger diameter ball portion 54 and integrating the smaller diameter ball portion 56 sufficiently reduces the height of the expanding ball portion so that the cavity can fall within the preferred depth limits discussed above.

The mounting cavity 20 includes a radial lip or ring 62 at the opening of the cavity adjacent the platform surface 14. As the ball portion 36 expands, the larger ball portion 54 contacts this lip at point $P_1$. It is understood that this point $P_1$ represents a circumferential line of contact between the spherical ball portion 54 and the cylindrical cavity 20. As the larger ball portion 54 expands further into the lip 62, the reaction pushes the ball portion 36 deeper into the cavity 20 until the smaller ball portion 56 bottoms on the cavity base 58 at point $P_2$. Again, it is understood that the point of contact $P_2$ represents a circumferential line of contact between the spherical ball portion 56 and the flat base 58, broken at 90° intervals by the gaps formed by the expanded slots 42. Further expansion of the larger ball portion 54 stops when the portion contacts the cavity side wall 60 at the circumferential point of contact $P_3$. These three points of contact $P_1$, $P_2$, and $P_3$ fix the location of the center of rotation C and provide a solid engagement of the ball portion 36 within the cavity 20.

In a specific embodiment of the invention, the larger ball portion 54 is formed at a spherical diameter of 0.364 inches, while the smaller ball portion has a spherical diameter of 0.314 inches. The expansion slots 42 have a width of 0.025 inches. The expansion slots also accommodate compression of the ball portion 36 so that the inner diameter of the lip 62 can be smaller than the spherical diameter of the larger ball portion. In other words, in the specific embodiment, the cylindrical wall 60 of the cavity 20 is formed at a diameter of about 0.375, which is greater than the largest diameter of the expanding ball portion 36. The lip 62 projects inward from the cavity side wall 60 at an inner diameter of about 0.355 inches, which is less than the diameter of the larger ball portion 54. When the slots 42 are fully compressed, the diameter of the larger ball portion decreases by about ½ the slot width, or by about 0.012 inches. This reduced outer diameter of 0.352 inches is less than the inner diameter of the lip so that compressed ball portion can slide past the lip 62 and into the cavity 20. Once inside, the ball portion 36 is restored to its normal size so that the cylinder portion 34 is loosely retained on the trial broach 12.

Figure 6:
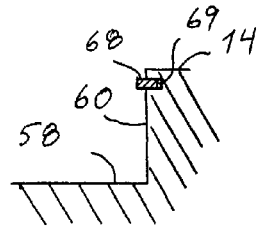
FIG. 6 is an enlarged cross-section view of an alternative embodiment of the mounting cavity for receiving the trial ball cylinder.

In the preferred embodiment, the lip 62 is integrally formed within the cavity 20, such as by machining an undercut in the trial broach 12. Alternatively, the circumferential lip can be created by a snap-ring 68 mounted within a groove 69 adjacent the platform surface 14, as shown in FIG. 6. The snap-ring projects inward into the interior of the cavity to define an inner diameter comparable to the inner diameter of the lip 62 shown in FIG. 5. The snap ring preferably bottoms within the groove so that there is no variation in the inner diameter defined by the ring, which is important to ensure proper positioning of the center of rotation C.

Figure 3:
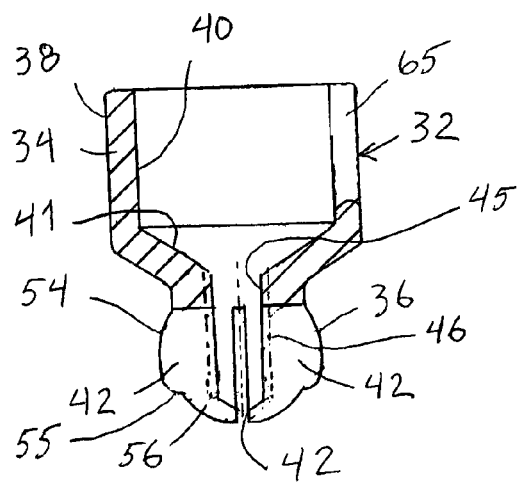
FIG. 3 is a cross-sectional view of a ball cylinder of the trial assembly shown in FIG. 2.
Figure 4:
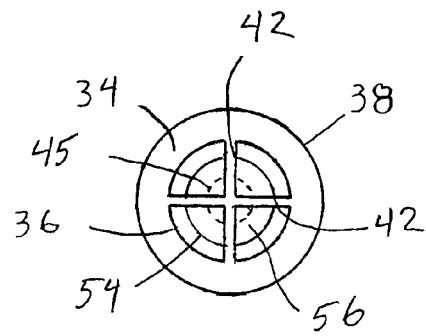
FIG. 4 is a bottom view of the ball cylinder shown I FIG. 3.

In the embodiment of FIGS. 2-4, the expanding ball portion 36 relies upon a tapered threaded bore and an expansion screw to expand the ball portion and lock it within the cavity.

Figure 7:
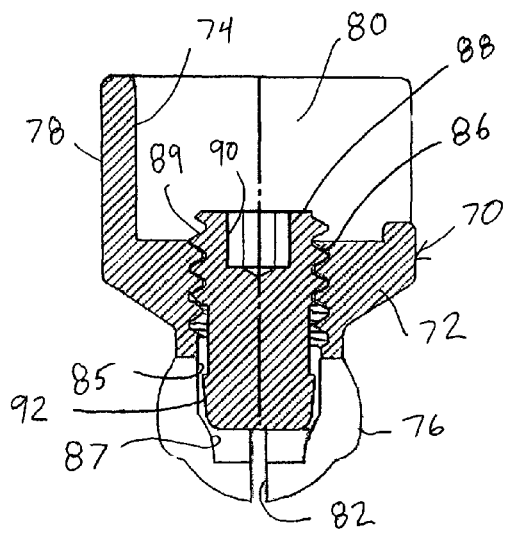
FIG. 7 is an enlarged cross-section view of a ball cylinder according to another embodiment of the invention for use with the humeral implant shown in FIG. 1.

In an alternative embodiment, a peg and cam approach is used to expand the ball portion. As shown in FIG. 7, a trial assembly 70 includes a trial ball cylinder 72 having a cylindrical portion 74 and an expanding ball portion 76. The cylindrical portion 74 has an outer surface 78 that is adapted to mate with the bore 17 in the humeral head component 16. The cylindrical portion also defines an inner cavity 80 and the ball portion 76 includes expansion slots 82 similar to the prior embodiment.

In this embodiment, the cavity 80 opens into a bore 85 passing through the expanding ball portion 76. The upper portion of the bore bears internal threads 86, while the lower portion of the bore defines a circumferential cam surface 87. As can be seen in FIG. 7, the cam surface is inwardly curved relative to the bore 85. The expansion element is a screw 88 having an upper threaded portion 89 configured to mate with the internal threads 86. A hex recess 90 accepts a hex driving tool to thread the expansion element into the bore.

The lower portion of the screw 88 defines a peg 92 that bears against the cam surface 87 as the screw is driven into the bore. In the preferred embodiment, the peg is tapered, as shown in FIG. 7. As the peg traverses the cam surface it expands the surface, and ultimately expands the slots 82 in the same manner as described above to lock the ball portion 76 within the cavity 20.

It can be appreciated that the present invention contemplates a trial assembly, such as the assemblies 30 and 70, which allow a full range of articulation or rotation of the trial components, and more specifically the trial head component 16. The expanding ball portions 36, 76 positively establish the center of rotation C, which coincides with the origins for the larger and smaller spherical ball portions. As with other trial implants, the trial broach 10 is positioned within the prepared IM canal with the platform surface 14 aligned with the resected surface of the humerus bone. The trial ball cylinder 32 is then positioned within the mounting cavity 20. The three-dimensional angle of the trial cylinder relative to the broach stem can be adjusted with the trial humeral head 16 mounted on the cylinder portion 34. Once the trial head is properly oriented relative to the glenoid aspect of the shoulder joint, the expansion element 48, 88 is tightened using an appropriate tool. The mating bore 17 of the trial head 16 preferably passes through the head so that the expansion element can be accessed by the driving tool with the trial head in position on the cylinder portion. The interdigitating notch 65 and tab 66 help hold the trial head in position as the head is manipulated and the expansion element tightened.

In accordance with one aspect of the method of the present invention, the expansion element is tightened within the expanding ball portion without the application of an impaction force. In the preferred embodiment, the expansion element is tightened by applying torque or a rotational force to the element. Most preferably, a threaded interface is provided between the expansion element and the expanding ball portion so that the amount of tightening torque can be controlled. In an alternative approach, the rotational interface can be in the form of a bayonet engagement in which the expansion element is rotated through a fixed angle and mating cam surfaces propel the expansion end of the element into the bore of the expanding ball portion. With this alternative, the amount of rotation of the expansion element is calibrated so that the ball portion expands enough to ensure a solid fixation within the mounting cavity.

Figure 8:
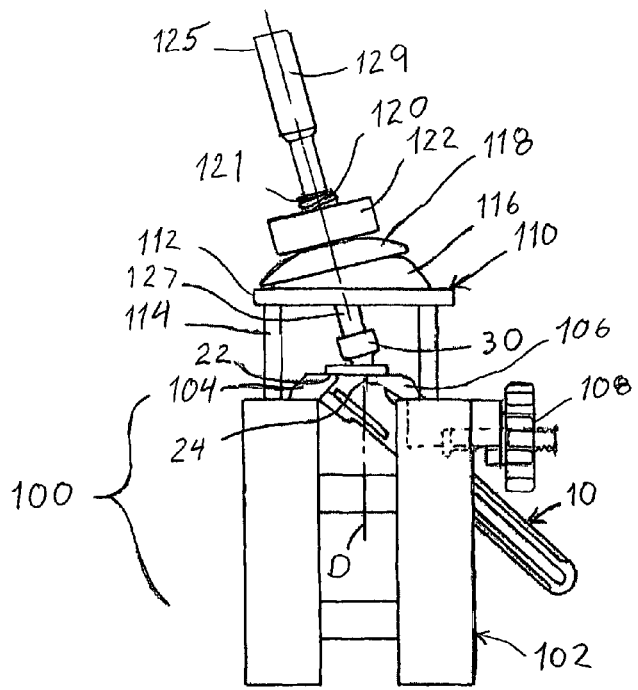
FIG. 8 is a side view of a replication instrument for use in replicating the angular orientation of the ball cylinder in the trial assembly of the present invention.

Once the angular orientation of the trial ball cylinder 32, 72 has been established, the entire trial broach is removed from the humerus bone. The trial assembly 30, 70 may then be mounted within a replication instrument to ascertain the angular position of the prosthetic head relative to the fixed datum D and established center of rotation C. Any replication instrument may be used to ascertain this orientation and translate that position to a final prosthesis. One exemplary replication instrument 100 shown in FIG. 8 is particularly suited for use with the trial assemblies 30 and 70 described above. The details of this instrument are disclosed in co-pending application Ser. No. 10/879,261 (the '261 application), entitled INSTRUMENTATION FOR RECORDING AND REPLICATING ORTHOPAEDIC IMPLANT ORIENTATION, owned by the assignee of the present invention, the disclosure of which is incorporated herein by reference.

As described in the '261 application, the instrument 100 includes a base assembly 102 that carries a stationary clamp element 104 and a movable clamp element 106. An adjustment mechanism 108 may be manually operated to move the movable clamp element toward the stationary element 104. As explained above, the neck 13 of the trial broach 10 (as well as the final humeral implant) is provided with positioning grooves 22 and 24. The superior groove 22 accepts the fixed clamp element 104, while the pair of inferior grooves 24 are configured to mate with the movable clamp element 106. When the neck of the trial broach is engaged by the clamp elements 104, 106, the position of the datum D is fixed at a known orientation.

The replication instrument 100 further includes a replication fixture 110 that is mounted on the base assembly 102. The fixture includes a platform 112 with legs 114 that are supported on the base assembly. The platform 110 includes an annular dome 116 which supports a spherical washer 118 on one surface and a cannulated guide member 120 on the opposite surface. The guide member includes a hollow stem portion 121 that passes through the dome 116 and washer 118. The stem portion 121 is threaded to receive a locking nut 122 to fix the angular orientation of the guide member 120 relative to the datum D.

As explained in more detail in the '261 application, the guide member 120 cannula allows passage of an alignment tool 125, and more particularly the guide shaft 127 of the tool. The distal end of the guide shaft is sized to fit snugly within the cavity 40, 80 of the cylinder portion 34, 74. When the guide shaft 127 is situated within the cylinder portion of the trial assembly, the guide member 120 and spherical washer 118 assume a corresponding spatial angle relative to the dome 116. At this point in the method, the locking nut is tightened, thereby fixing the three-dimensional angular position of the guide member 120. The replication fixture 110 is then removed and the trial broach 10 released from the base assembly. The final humeral prosthesis is then clamped within the base assembly with a final head mounting assembly loosely engaged to the final implant stem. The alignment tool is reinserted into the guide member and the guide shaft is engaged with the mounting assembly to replicate the angular orientation of the trial ball cylinder 32, 72. The alignment tool 125 is configured with an impaction end 129 that can be struck with a mallet to impact the final implant mounting assembly within the final implant stem. Once the humeral head is impacted onto the mounting assembly, the prosthesis is ready to be implanted in the humerus bone.

It can be appreciated that with the present invention, all of the impaction steps occur outside the patient's body and with the use of separate fixtures. Thus, the invention allows for highly accurate replication of the appropriate anatomic angle for the humeral head relative to the humerus and glenoid aspects of the shoulder joint. These same principles can be used for other joint prostheses where the angle of an articulating component is critical.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A trial implant for a joint of a patient, comprising:
a stem component configured for placement within a bone of a patient;
an articulating component configured for articulating contact with a mating aspect of the joint; and
a mounting assembly for mounting the articulating component to the stem component at variable angular orientations relative thereto, including;
a cavity defined in the stem component;
a mounting element having a portion configured to support the articulating component and an expandable portion configured to expand within said cavity; and
an expansion element rotatable within said mounting element and cooperating with said expandable portion upon rotation to expand said expandable portion within said cavity;
wherein said expandable portion of said mounting element includes an expanding ball, and a bore within said ball;
wherein mating portions of said expansion element and said bore define a rotational engagement so that rotation of said expansion element drives said expansion element into said bore;
wherein said expansion element and said bore include cooperating portions that cooperate to expand said ball when said expansion element is driven into said bore; and
wherein said expanding ball includes a first ball portion adjacent said portion of said mounting element configured to support the articulating component and defining a first spherical diameter, and a second ball portion defining a second spherical diameter smaller than said first spherical diameter.

2. The trial implant of claim 1, wherein:
said bore is a tapered threaded bore; and
said expansion element is a screw configured to be threaded into said threaded bore.

3. The trial implant of claim 1, wherein:
said mating portions define a threaded engagement; and
said cooperating portions include a tapered portion of said bore and a peg on said expansion element sized to expand said tapered portion when said expansion element is driven into said bore.

4. The trial implant of claim 1, wherein said cavity includes an annular rim extending into said cavity.

5. The trial implant of claim 4, wherein said annular rim defines an inner diameter that is less than the outer diameter of said expandable portion of said mounting element in its unexpanded state.

6. The trial implant of claim 5, wherein said expandable portion has a compressed state defining an outer diameter less than said inner diameter so that said expandable portion can be inserted past said annular rim into said cavity.

7. The trial implant of claim 4, wherein said annular rim defines an inner diameter that is less than the outer diameter of said expandable portion of said mounting element in its expanded state.

8. A trial implant, comprising:
a stem component having a cavity defining a cavity bottom surface and a cavity side wall and including a lip that extends into said cavity, said lip defining an access opening for said cavity;
a head component having a coupling member;
a mount having a first connector portion configured to be received in said cavity and a second connector portion configured to cooperate with said coupling member of said head component to connect said mount to said head component, said first connector portion including an expandable member configured to be received within said cavity, and said expandable member having (i) a first ball portion connected to said second connector portion and defining a first spherical diameter, and (ii) a second ball portion connected to said first ball portion and defining a second spherical diameter that is smaller than said first spherical diameter; and
an actuator configured to be received within said expandable member so as to expand said expandable member within said cavity,
wherein, when said actuator is received within said expandable member to expand said expandable member within said cavity, (i) said first ball portion contacts said lip, and (ii) said second ball portion contacts said cavity bottom surface.

9. The trial implant of claim 8, wherein:
said first ball portion includes a first proximal end and a first distal end,
said second ball portion includes a second proximal end and a second distal end,
said first proximal end of said first ball portion is connected to said second connector portion, and
said first distal end of said first ball portion is connected to said second proximal end of said second ball portion.

10. The trial implant of claim 9, wherein:
when said actuator is received within said expandable member to expand said expandable member within said cavity, said distal end of said second ball portion contacts said cavity bottom surface.

11. The trial implant of claim 8, wherein:
said mount has a threaded bore defined therein,
said actuator includes a threaded shaft, and
said threaded shaft cooperates with said threaded bore to receive said actuator within said mount to expand said expandable member.

12. The trial implant of claim 8, wherein:
said head component defines a second cavity,
said coupling member of said head component includes a cylindrical inner surface defined by said second cavity,
said second connector portion of said mount includes an attachment member defining a cylindrical outer surface, and
said cylindrical outer surface is positioned in contact with said cylindrical inner surface.

13. A trial implant, comprising:
a stem component defining a cavity;
a head component having a coupling member; and
a mount having a first connector portion configured to be received in said cavity and a second connector portion configured to cooperate with said coupling member of said head component to connect said mount to said head component, said first connector portion including an expandable member configured to be received within said cavity, and said expandable member having (i) a first ball portion connected to said second connector portion and defining a first spherical diameter, and (ii) a second ball portion connected to said first ball portion and defining a second spherical diameter that is different from said first spherical diameter; and an actuator configured to cooperate with said expandable member so as to expand said expandable member within said cavity.

14. The trial implant of claim 13, wherein:

said stem includes a lip projecting into said cavity, said cavity is defined by a cavity bottom surface and a cavity side wall, and when said actuator is received within said expandable member to expand said expandable member within said cavity, (i) said first ball portion contacts said lip, and (ii) said second ball portion contacts said cavity bottom surface.

15. The trial implant of claim 14, wherein said lip defines an access opening for said cavity.

16. The trial implant of claim 13, wherein:

said head component defines a second cavity, said coupling member of said head component includes a cylindrical inner surface defined by said second cavity, said second connector portion of said mount includes an attachment member defining a cylindrical outer surface, and said cylindrical outer surface is positioned in contact with said cylindrical inner surface.

17. The trial implant of claim 13, wherein said first spherical diameter is larger than said second spherical diameter.

18. The trial implant of claim 13, wherein:

said first ball portion includes a first proximal end and a first distal end, said second ball portion includes a second proximal end and a second distal end, said first proximal end of said first ball portion is connected to said second connector portion, and said first distal end of said first ball portion is connected to said second proximal end of said second ball portion.

19. The trial implant of claim 18, wherein:

said stem includes a lip projecting into said cavity, said cavity is defined by a cavity bottom surface and a cavity side wall, and when said actuator cooperates with said expandable member to expand said expandable member within said cavity, (i) said first ball portion contacts said lip, and (ii) said distal end of said second ball portion contacts said cavity bottom surface.

20. The trial implant of claim 13, wherein:

said mount has a threaded bore defined therein, said actuator includes a threaded shaft, and said threaded shaft cooperates with said threaded bore to receive said actuator within said mount to expand said expandable member.

* * * * *